United States Patent [19]

Costain et al.

[11] 4,310,464
[45] Jan. 12, 1982

[54] LACTONES

[75] Inventors: Winston Costain; Bernard W. H. Terry, both of Manchester; Nazim Punja, Wokingham; Peter J. V. Cleare, Ascot, all of England

[73] Assignee: Imperial Chemical Industries Limited, London, England

[21] Appl. No.: 702,732

[22] Filed: Jul. 6, 1976

[30] Foreign Application Priority Data

Jul. 11, 1975 [GB] United Kingdom ............... 29253/75

[51] Int. Cl.³ ............................................. C07D 307/32
[52] U.S. Cl. ............................. 260/343.6; 260/544 Y; 560/124; 560/226; 560/228
[58] Field of Search ...................................... 260/343.6

[56] References Cited

U.S. PATENT DOCUMENTS 3,488,732 1/1970 Heiba et al. ...................... 260/343.6
3,758,514 9/1973 Heiba et al. ...................... 260/343.6
3,813,416 5/1974 Heiba et al. ...................... 260/343.6

OTHER PUBLICATIONS

Finkbeiner et al., Ox. of Acetic Acid by $Mn^{+3}$ Salts (8-68).
Heiba et al., J.A.C.S. 96: 26, pp. 7977-7981 (1974).
Finkbeiner et al., C.A. 72: 89803w (1970).

Primary Examiner—Norma S. Milestone
Attorney, Agent, or Firm—Cushman, Darby & Cushman

[57] ABSTRACT

4-$\beta$, $\beta$-dichlorovinyl (or dibromovinyl)-3,3-dimethyl-butyrolactones are prepared from 1,1-dichloro (or dibromo)-4-methylpenta-1,3-diene by reacting with an acid of formula $CH_2R.CO_2H$ in presence of a salt of a metal in one of its higher valency states, especially manganese (III), cerium (IV), or vanadium (V). Higher yields are obtained in the presence of the anhydride of the acid and of the sodium or potassium salt of the acid. Treatment of the lactones with an inorganic acid halide opens the lactone ring with formation of the corresponding 4-haloacid halide, which with alcohols affords the corresponding 4-haloacid ester, cyclised by bases to a 3-$\beta,\beta$-dichloro (or dibromo)vinyl-2,2-dimethylcyclopropanecarboxylic ester, intermediate for insecticides such as the m-phenoxybenzyl ester.

1 Claim, No Drawings

LACTONES

This invention relates to lactones and more particularly to certain γ-butyrolactones of value as intermediates for the manufacture of insecticides.

Esters, such as the m-phenoxybenzyl ester, of 3-β,β-dichlorovinyl-2,2-dimethylcyclopropane-carboxylic acid are valuable insecticides. It has now been found that 4-β,β-dichlorovinyl-3,3-dimethylbutyrolactones and the corresponding dibromo compounds, which can be easily prepared from readily available starting materials, can be converted into 3-β,β-dichloro or dibromo vinyl-2,2-dimethylcyclopropanecarboxylic acid or esters of these with e.g. lower alcohols from which the insecticidal esters can be obtained.

According to the invention there are provided lactones of the formula:

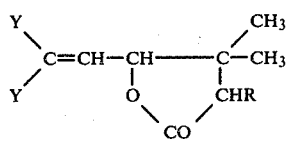 (I)

wherein each Y is a chlorine or bromine atom and R is a hydrogen atom, a cyano or carboxy group or an optionally substituted alkyl group.

Where R is not a hydrogen atom the lactone may be the cis or trans isomer or mixtures of these.

As optionally substituted alkyl groups which may be represented by R there may be mentioned methyl, ethyl, isopropyl, n-propyl, tert,-butyl, n-butyl, carboxymethyl or cyanomethyl.

According to the invention there is also provided a process for the manufacture of lactones of formula I which comprises reacting 1,1-dichloro(or dibromo)-4-methylpenta-1,3-diene with an acid of the formula $CH_2R.CO_2H$, in which R has the significance given above, in presence of a salt of a metal in one of its higher valency states.

As metals there may be mentioned metals having at least two valency states, the higher valency state used in the reaction being for example manganese (III), cerium (IV) and vanadium (V). The metal may be used as a salt of the acid of formula $CH_2R.CO_2H$, or may be for example in the form of metal oxide. Alternatively the metal may be present in the anion of the salt.

The salt may be added having the metal in the desired higher valency state, or a salt of the metal in a lower valency state may be used and oxidised in situ, for example with potassium permanganate, to the desired higher valency state before introduction of the diene. Alternatively the required higher valency state may be achieved by e.g. electrochemical or selective oxidation methods during the reaction.

Salts of two or more metals may be used in conjunction if desired, for example salts of manganese and vanadium especially using only small proportions of vanadium.

The process of the invention may be carried out at a temperature preferably between ambient and 200° C. at atmospheric pressure, although increased pressure may be used if desired.

It is usually convenient to use an excess of the acid which also serves to dissolve the metal salt.

The metal salt is preferably used in amount sufficient to provide the equivalent of about one atom of oxygen, assuming the metal is reduced to its lower valency state, for each mol. of diene.

The acid may be for example acetic or propionic acid or may be a substituted acid such as cyanoacetic acid or succinic acid. These substituted acids react more readily than e.g. acetic acid in the process. Improved yields are usually obtained by the addition of a salt, for example sodium or potassium salt, of the acid.

It is preferred to carry out this reaction under an inert atmosphere, such as nitrogen, and in substantial absence of water which may conveniently be brought about by addition of the anhydride of the acid.

If desired the reaction may be carried out in an inert solvent, for example acetonitrile, adiponitrile, tetrahydrofuran or dimethylsulphoxide.

The lactone may be isolated by conventional means, for example evaporation of excess of the acid, preferably under reduced pressure, addition of water and extraction of the product in a water-immiscible solvent. Removal of the solvent leaves crude product which may be purified by distillation under reduced pressure.

The lactone may contain minor amounts of an isomeric lactone in which the —O—CO—CHR— group is attached to the remainder of the molecule the reverse way round, i.e. with the oxygen atom attached directly to the carbon atom carrying the two methyl groups. It is not necessary to remove this impurity if the lactone is to be used in the second process of the invention.

According to the invention there is further provided a second process by which esters of the formula:

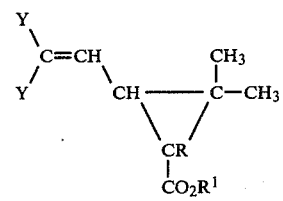

wherein $R^1$ is an optionally substituted alkyl group and R and Y have the meanings given hereinbefore are prepared by treating a lactone of formula I with an acid chloride or bromide and treating the product with an alcohol of the formula $R^1OH$ and a base.

This second process proceeds in three stages which may be carried out if desired, especially in respect of the first and second stages, without isolation of the intermediate products. Each individual stage, and the two combinations of successive stages, are also features of the invention.

In the first stage of the process the lactone ring is opened and the appropriate 3,3-dimethyl-4-chloro (or bromo)-6,6-dichloro (or dibromo)hex-5-enoyl chloride (or bromide) is obtained. In this stage it is preferred that R be a hydrogen atom or optionally substituted alkyl group.

The first stage of the process is conveniently carried out using at least a molar amount, and preferably not more than 1.5 molar amounts, of acid chloride or bromide at a temperature between ambient and the boiling point of the reaction mixture.

As acid chlorides or bromides there may be mentioned especially inorganic acid chlorides such as thionyl chloride, phosphorous pentachloride and phosphorus oxychloride, which provide hexenoyl chloride having a 4-chloro substituent, and inorganic acid bromides such as thionyl bromide and phosphorus pentabromide, which provide acid bromides having a 4-bromo substituent.

The second stage of the process, treatment with the alcohol of the formula R$^1$OH, is preferably carried out without isolation of the product of the first stage. The alcohol is preferably used in excess, for example 1.5 molar proportions, and a reaction temperature from ambient to the boiling point of the reaction mixture may conveniently be used. The alcohol, R$^1$OH, is preferably a lower alkyl alcohol, especially methanol or ethanol.

The product of the second stage, the ester of the acid of which the acid chloride resulted from the first stage, may if desired be isolated by conventional means, for example removal of excess alcohol, R$^1$OH, and distillation under reduced pressure, but it is not usually necessary to carry out such isolation before carrying out the third stage.

The third stage, treatment with the base, may be carried out at a temperature between ambient and the boiling point of the reaction mixture using a solvent conveniently the alcohol, R$^1$OH. The base is preferably an alkali metal alkoxide, for example NaOR$^1$, but may be another alkoxide or sodium hydroxide in ethanol.

The amount of base is preferably from 2.0 to 3.0 molar equivalents.

The cyclopropanecarboxylic ester may be isolated by conventional means, for example neutralisation by the addition of e.g. dilute sulphuric acid, separation from the residue of any salt, removal of excess alcohol by distillation, addition to water and extraction with a water-immiscible solvent. After removal of the solvent the product may be purified by distillation under reduced pressure.

The cyclopropanecarboxylic ester may be converted into an insecticidal ester by known means, for example an ester interchange reaction with e.g. m-phenoxybenzyl alcohol using a catalyst such as potassium tert,-butoxide or may be converted into for example the corresponding acid or acid chloride which may then be esterified with e.g. m-phenoxybenzyl alcohol.

The process of the invention, providing the lactones of the invention, followed by the further process of the invention and introduction of an appropriate esterifying group afford a route to insecticidal esters of 3-$\beta,\beta$-dichloro(or dibromo) vinyl-2,2-dimethylcyclopropane-2-carboxylic acids which has fewer stages and gives higher yields than the routes hitherto described or used.

The invention is illustrated but not limited by the following examples in which all parts and percentages are by weight unless stated otherwise.

EXAMPLE 1

53 g of manganous acetate tetrahydrate were dissolved in 3000 ml. of acetic acid and stirred at 90° C. under a nitrogen atmosphere. 8.0 g of potassium permanganate were added slowly. When the addition was complete 75 ml. of acetic anhydride, 125 g. of anhydrous sodium acetate were added followed by 22.6 g. of 1,1-dichloro-4-methyl-pentadiene-1,3. The mixture was stirred at the boiling point (125° C.) until the brown colour (manganic salt) was discharged (about 2.5 hours), cooled to room temperature and filtered to remove sodium acetate. The sodium acetate was washed with acetic acid. The filtrate and washings were combined, heated under reduced pressure to remove acetic acid, dissolved in water and extracted with ether. The ether extract was washed with saturated sodium carbonate solution, dried, and the ether distilled off. The residues thus obtained from the experiments were combined and fractionated to give 16.1 g. of mean fraction, boiling at 89°–112° C. at a pressure of 0.25 mm. of mercury and containing approximately 67% of 2-$\beta,\beta$-dichlorovinyl-3,3-dimethyl-5-oxotetrahydrofuran, identified by mass spectroscopy, which gave m/e 208, and infra red spectroscopy, which gave a main absorption based at 1780 cm$^{-1}$ elastomeric of a lactone.

EXAMPLE 2

500 ml. of acetic acid, 150 g. of anhydrous potassium acetate, 25 ml. of acetic anhydride and 23.4 g. of ammonium vanadate were stirred at the boiling point under nitrogen. 15.1 g. of 1,1-dichloro-4-methyl-pentadiene were added over 30 minutes and the mixture maintained at the boiling point for 5 hours during which time the colour changed from green to blue. The mixture was then evaporated under reduced pressure, dissolved in water, and extracted with ether. The ether extract was washed with dilute sodium hydroxide solution, dried, and distilled to give impure 2-$\beta,\beta$-dichlorovinyl-3,3-dimethyl-5-oxotetrahydrofuran, which after analysis by gas-liquid chromatography indicated a conversion of 10–15%.

EXAMPLE 3

The procedure of Example 1 was repeated but all the manganese was added as potassium permanganate (30 g.) and the sodium acetate was omitted. A similar product was obtained.

EXAMPLE 4

200 Parts of acetic acid and 75 parts of manganous acetate tetrahydrate were heated with agitation to 80° C. 14 Parts of potassium permanganate were then added portionwise to the mixture (there was an exothermic reaction). The mixture was stirred at 80°–85° C. for 10 minutes. 300 Parts of acetic anhydrate were added and the temperature rose to 120° C. The mixture was cooled to 100° C. 15.1 Parts of 1,1-dichloro-4-methylpenta-1,3-diene were added at 100° C. and the mixture stirred at 100° until the colour changed to a pale brown (about 40 minutes were required). The suspension was boiled for 1 hour and then cooled to room temperature and stirred for a further 1 hour.

The cold suspension was filtered, the precipitate being washed with 2×50 parts of acetic acid. The acetic acid was removed from the combined filtrate and washings, water added and the whole extracted with ether. On evaporation a residue was obtained which contained 29.5% of 2-($\beta,\beta$-dichlorovinyl)-3,3-dimethyl-5-oxotetrahydrofuran.

EXAMPLE 5

250 Parts of acetic acid and 250 parts of acetic anhydride were mixed and stirred at 90° C. and 15.1 parts of 1,1-dichloro-4-methylpenta-1,3-diene and 80 parts of manganic acetate dihydrate were then added simultaneously at 90°–94° over 55 minutes. The reaction mixture was stirred at 90°–94° until the colour changed to a pale brown (which required about 10 minutes). The reaction was then stirred at 90°–94° for a further 20 minutes, cooled to room temperature and stirred for 1 hour. The precipitate was filtered and washed with 2×50 parts of acetic acid. The acetic acid was then removed from the combined filtrate and washings under reduced pressure to leave a residue containing 34.8% of 2-($\beta,\beta$-dichlorovinyl)-3,3-dimethyl-5-oxotetrahydrofuran.

EXAMPLE 6

1.8 Parts of vanadium pentoxide were added with stirring at room temperature to 200 parts of acetic acid and the mixture stirred at room temperature for 5 minutes. 60 Parts of manganic acetate dihydrate and 250 parts of acetic anhydride were added to the mixture at room temperature and the mixture stirred for a further 10 minutes. The mixture was heated to 100° C. and 15.1 parts of 1,1-dichloro-3,3-dimethyl-4-methyl-penta-1,3-diene were added. The reaction mixture was stirred at 100° C. until the colour changed to beige (this required about 30 minutes). The reaction was cooled to room temperature and stirred for a further 1 hour. The precipitate was removed by filtration and washed with 2×50 parts of acetic acid. The acetic acid was removed from the combined filtrate and washings, water was added and the whole extracted with ether. On evaporation a residue was obtained which contained 28.2% of 2-($\beta,\beta$-dichlorovinyl)-3,3-dimethyl-5-oxotetrahydrofuran.

EXAMPLE 7

29.08 Parts of thionyl chloride were added dropwise with stirring at room temperature to 20.8 parts of 2-($\beta,\beta$-dichlorovinyl)-3,3-dimthyl-5-oxotetrahydrofuran. The mixture was boiled for 1 hour after which the unreacted thionyl chloride was distilled off to give crude 3,3-dimethyl-4,6,6-trichlorohex-5-enoyl chloride.

20 Parts of ethanol were then added dropwise, the temperature being maintained at below 30° C. and the mixture was then refluxed for 1 hour. The product was distilled under reduced pressure giving 15.28 parts of ethyl 4,4,6-trichloro-3,3-dimethylhex-5-enoate, which contained a minor amount of unchanged lactone.

EXAMPLE 8

A slurry of 11.2 parts of potassium t-butoxide in 200 parts of toluene was added slowly to 13.7 parts of ethyl 4,6,6-trichloro-3,3-dimethyl-hex-5-enoate stirred at below 0° C. and stirred at below 0° C. for a further 1 hour. The mixture was neutralised to pH 6 with concentrated hydrochloric acid. Water was added to dissolve the precipitated salt and the toluene layer separated. The water layer was extracted again with toluene and the toluene then removed from the combined extracts giving in nearly theoretical yield the mixed cis and trans forms of ethyl 3-$\beta,\beta$-dichlorovinyl-2,2-dimethylcyclopropanecarboxylate.

We claim:
1. A lactone of the formula:

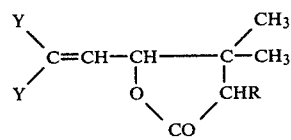

wherein each Y is chlorine or bromine and R is hydrogen.

* * * * *